(12) United States Patent
Krol et al.

(10) Patent No.: US 8,691,987 B2
(45) Date of Patent: Apr. 8, 2014

(54) METHOD OF PRODUCING POLYMERIC PHENAZONIUM COMPOUNDS

(76) Inventors: Andrew M. Krol, Bristol, CT (US); Ernest Long, Burlington, CT (US); Lev Taytsas, Naugatuck, CT (US)

(*) Notice: Subject to any disclaimer, the term of this patent is extended or adjusted under 35 U.S.C. 154(b) by 633 days.

(21) Appl. No.: 12/890,013

(22) Filed: Sep. 24, 2010

(65) Prior Publication Data

US 2012/0077956 A1  Mar. 29, 2012

(51) Int. Cl.
*C07D 241/46* (2006.01)

(52) U.S. Cl.
USPC .......... 544/347; 528/423; 205/277; 205/279; 205/297; 205/310; 205/312; 205/423

(58) Field of Classification Search
USPC .......... 544/347; 528/423; 205/277, 279, 297, 205/307, 310, 312, 423
See application file for complete search history.

(56) References Cited

U.S. PATENT DOCUMENTS

| | | | |
|---|---|---|---|
| 3,743,584 A | 7/1973 | Todt et al. | |
| 3,956,084 A | 5/1976 | Kardos et al. | |
| 4,567,252 A * | 1/1986 | Buhler et al. | 534/882 |
| 5,433,840 A | 7/1995 | Dahms et al. | |
| 2006/0226021 A1 | 10/2006 | Brunner et al. | |

FOREIGN PATENT DOCUMENTS

| | | |
|---|---|---|
| EP | 1 592 825 | 3/2009 |
| GB | 1 357 442 | 6/1974 |

\* cited by examiner

*Primary Examiner* — Shane Fang
(74) *Attorney, Agent, or Firm* — Carmody Torrance Sandak & Hennessey LLP

(57) ABSTRACT

A process of making a polymeric phenazonium compound having the general formula:

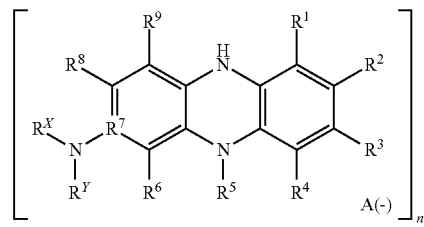

wherein $R^1$, $R^2$, $R^4$, $R^5$, $R^6$, $R^8$ and $R^9$ are the same or different, and represent hydrogen, a low alkyl or a substituted aryl, $R^3$ starts with $NH_2$ and is diazotized followed by polymerization, $R^5$ and $R^8$ may alternatively represent monomeric or polymeric phenazonium radicals, $R^7$ with its substituent group is a substituted amine, with $R^X$ and $R^Y$ representing any combination of $CH_3$, $C_2H_5$,

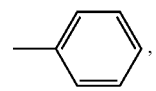

, and hydrogen, except that $R^X$ and $R^Y$ cannot both be hydrogen, A is an acid radical, and n is an integer from 2 to 100, preferably from 2 to 20 is described. The polymeric phenazonium compound is usable in as an additive in a metal plating bath. The method includes the steps of: a) dissolving an effective amount of an amino compound in a formic acid solution; b) adding a nitrite salt to diazotize the amino compound; and c) adding sulfamic acid to neutralize any excess nitrous acid that may be formed in step b), whereby a polymeric phenazonium compound is produced.

6 Claims, No Drawings

METHOD OF PRODUCING POLYMERIC PHENAZONIUM COMPOUNDS

FIELD OF THE INVENTION

The present invention relates generally to improved methods of producing polymeric phenazonium compounds.

BACKGROUND OF THE INVENTION

The addition of organic substances to acid copper electrolyte bath, including for example, copper sulfate electrolytes, has been well known in the art for depositing bright copper layers instead of a crystalline matte deposit. These additives include, for example, polyethylene glycol, thiourea and derivatives thereof, thiohydantoin, thiocarbaminic acid ester and thiophosphoric acid ester, safraninines, thiourea-formaldehyde condensates and certain C=S compounds. The foregoing additives have traditionally been used as additives for acid copper electrolytes, including copper sulfate electrolytes, to obtain bright copper coatings. In addition, polymeric phenazonium compounds have also been developed for use in acid copper electrolytes for depositing bright, level copper coatings and can be used alone or in combination with these other organic substances.

As described for example in U.S. Pat. No. 3,743,584 to Todt et al., the subject matter of which is herein incorporated by reference in its entirety, a polymeric phenazonium compound may be prepared by diazotizing an amino solution in an acid solution and subsequently boiling down of the resulting diazonium salt.

The diazotization of the amino compound is typically accomplished by suspending the monomer in a solution of a strong acid, such as sulfuric acid, hydrochloric acid, acetic acid, fluoroboric acid, phosphoric acid and/or another suitable acid. The acids form the diazonium acid radical. Boiling down of the formed diazonium salt takes place at a temperature that is typically within the range of about 5 to 100° C., preferably about 10 to 25° C. The reaction products precipitate from the acid reaction solution or can be precipitated therefrom by neutralization with a base such as ammonia or a hydroxide, such as potassium hydroxide.

Polymeric phenazonium compounds prepared in accordance with this process typically have the general formula:

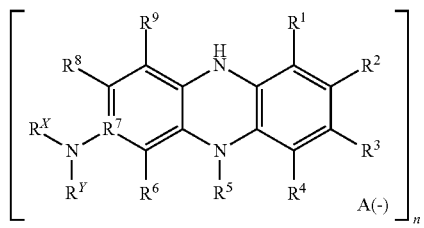

wherein $R^1$, $R^2$, $R^4$, $R^5$, $R^6$, $R^8$ and $R^9$ are the same or different, and represent hydrogen, a low alkyl or a substituted aryl, $R^3$ starts with $NH_2$ and is diazotized followed by polymerization, $R^5$ and $R^8$ may alternatively represent monomeric or polymeric phenazonium radicals, $R^7$ with its substituent group is a substituted amine with, $R^X$ and $R^Y$ representing any combination of $CH_3$, $C_2H_5$

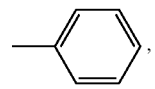

and hydrogen, except that $R^X$ and $R^Y$ cannot both be hydrogen, A is an acid radical, and n is an integer from 2 to 100.

As lower alkyl radicals, methyl, ethyl, and propyl may be used among others.

As aryl radicals, phenyl, which may be substituted by methyl, ethyl, methoxy, ethoxy, etc., among others may be used.

Examples of polymeric phenazonium compounds of this type include poly(6-methyl-7-dimethylamino-5-phenyl phenazonium sulfate); poly(2-methyl-7-diethylamino-5-phenyl phenazonium chloride); poly(2-methyl-7-dimethylamino-5-phenyl phenazonium sulfate); poly(5-methyl-7-dimethylamino phenazonium acetate); poly(2-methyl-7-anilino-5-phenyl phenazonium sulfate); poly(2-methyl-7-dimethylamino phenazonium sulfate); poly(7-methylamino-5-phenyl phenazonium acetate); poly(7-ethylamino-2,5-diphenyl phenazonium chloride); poly(2,8-dimethyl-7-diethylamino-5-p-tolyl-phenazonium chloride); poly(2,5,8-triphenyl-7-dimethylamino phenazonium sulfate); and poly(7-dimethylamino-5-phenyl phenazonium chloride), by way of example and not limitation.

While these polymeric phenazonium compounds continue to enjoy success as additives for copper electroplating baths, it is would be desirable to provide a process of making these polymeric phenazonium compounds that requires fewer steps and that produces an additive having a smaller quantity of unreacted monomer remaining in the end product than the production methods of the prior art.

SUMMARY OF THE INVENTION

It is an object of the present invention to provide an improved method of forming a phenazonium monomer that overcomes the deficiencies of the prior art.

It is another object of the present invention to provide a method of forming a phenazonium monomer with an improved synthesis of the polymer dye.

It is still another object of the present invention to provide a method of forming a polymeric phenazonium compound that requires fewer processing steps.

It is still another object of the present invention to provide a method of forming a polymeric phenazonium compound that contains a higher percentage concentration of polymerized material being present in the end product as compared with prior art methods.

To that end, the present invention relates generally to a process of making a polymeric phenazonium compound having the general formula:

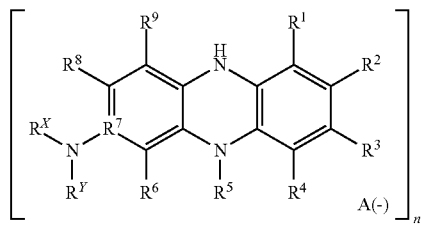

wherein $R^1$, $R^2$, $R^4$, $R^5$, $R^6$, $R^8$ and $R^9$ are the same or different, and represent hydrogen, a low alkyl or a substituted aryl, $R^3$ starts with $NH_2$ and is diazotized followed by polymerization, $R^5$ and $R^8$ may alternatively represent monomeric or polymeric phenazonium radicals, $R^7$ with its substituent group is a substituted amine, with $R^X$ and $R^Y$ representing any combination of $CH_3$, $C_2H_5$,

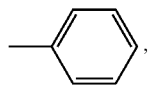

and hydrogen, except that $R^X$ and $R^Y$ cannot both be hydrogen, A is an acid radical, and n is an integer from 2 to 100, wherein said polymeric phenazonium compound is usable in as an additive in a metal plating bath, the method comprising the steps of:

a) dissolving an effective amount of an amino compound in a formic acid solution;

b) adding a nitrite salt to diazotize the amino compound; and c) adding sulfamic acid to neutralize any excess nitrous acid that may be formed in step b), wherein a polymeric phenazonium compound is produced.

DETAILED DESCRIPTION OF THE PREFERRED EMBODIMENTS

The present invention takes a different approach from the conventional approach for synthesizing polymeric phenazonium compounds described for example in U.S. Pat. No. 3,743,584, and appears to offer several advantages in the ease of synthesis of the polymer dye.

The present invention relates generally to polymeric phenazonium compounds and improved methods of making the same. These polymeric phenazonium compounds are used, for example in acid electrolytes for the deposition of bright, leveling copper coatings.

The inventors of the present invention have surprisingly found that both the amino compound and the resulting polymerized phenazonium dye are very soluble in a formic acid solution. While U.S. Pat. No. 3,743,584 indicates the use of acetic acid as a strong acid for producing polymerized phenazonium compounds, the use of acetic acid still requires the numerous steps set forth in this patent. However, the inventors of the present invention have found a surprising result when formic acid is used because of the solubility of the amino compounds in formic acid. Therefore, the result is that many fewer steps are required for producing polymeric phenazonium compounds by the process described herein.

In particular, it is possible to take the amino compound, dissolve the amino compound in a formic acid solution, and then add the nitrite in the usual manner at low temperature to diazotize the amino compound. Thereafter, sulfamic acid is added to neutralize any excess nitrous acid. The result is a highly concentrated solution of polymerized phenazonium dye that does not require any additional steps prior to use in the acid copper electrolyte solution and that takes the form:

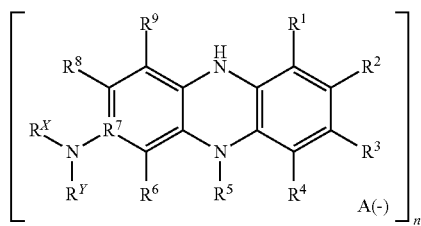

wherein $R^1$, $R^2$, $R^4$, $R^5$, $R^6$, $R^8$ and $R^9$ are the same or different, and represent hydrogen, a low alkyl or a substituted aryl, $R^3$ starts with $NH_2$ and is diazotized followed by polymerization, $R^5$ and $R^8$ may alternatively represent monomeric or polymeric phenazonium radicals, $R^7$ with its substituent group is a substituted amine with, $R^X$ and $R^Y$ representing any combination of $CH_3$, $C_2H_5$,

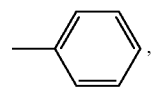

and hydrogen, except that $R^X$ and $R^Y$ cannot both be hydrogen, A is an acid radical, and n is an integer from 2 to 100.

More particularly, the present invention relates generally to a process of making a polymeric phenazonium compound as noted above wherein said polymeric phenazonium compound is usable in as an additive in a metal plating bath, the method comprising the steps of:

a) dissolving an effective amount of an amino compound in a formic acid solution at low temperature;

b) adding a nitrite salt to diazotize the amino compound; and c) adding sulfamic acid to neutralize any excess nitrous acid that may be formed in step b), whereby a polymeric phenazonium compound is produced.

Examples of amino compounds usable in the practice of the present invention include 2-methyl-3-amino-7-dimethylamino-5-phenyl-phenazonium sulfate, 3-amino-6-methyl-7-dimethylamino-5-phenyl-phenazonium hydrogen sulfate, 2-methyl-3-amino-7-diethylamino-5-phenyl-phenazonium chloride, 3-amino-7-dimethylamino-5-methyl phenazonium acetate, 2-methyl-3-amino-7-phenylamino-5-phenyl-phenazonium hydrogen sulfate, 2-methyl-3-amino-7-dimethylamino-phenazonium hydrogen sulfate, 3-amino-7-methylamino-5-phenylphenazonium acetate, 2-phenyl-3-amino-7-ethylamino-5-phenyl-phenazonium chloride, 1,2,6,9-tetramethyl-3-amino-7-diethylamino-5-phenyl-phenazonium hydrogen sulfate, 2,8-dimethyl-3-amino-7-diethylamino-5-tolyl-phenazonium chloride, and 2,9-diphenyl-3-amino-6-methyl-7-dimethylamino-5-phenyl-phenazonium hydrogen sulfate. These compounds most preferably have an amine in the three position and a substituted amine in the seven position.

In one preferred embodiment, the amino compound is 2-methyl-3-amino-7-dimethylamino-5-phenyl-phenazonium chloride, which has the structure:

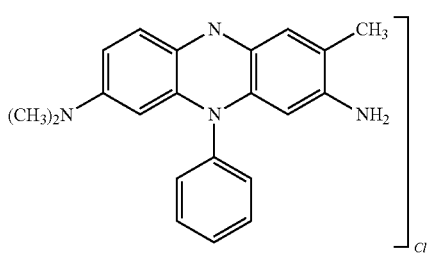

In another preferred embodiment, the amino compound is 2-methyl-3-amino-7-diethylamino-5-phenyl phenazonium chloride, which has the structure:

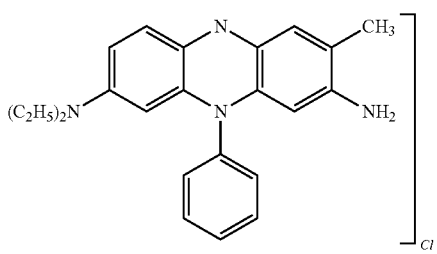

Based thereon, the polymeric phenazonium compounds produced from these amino compounds in accordance with the process described herein include compounds selected from the group consisting of polymeric phenazonium compounds of this type include poly(6-methyl-7-dimethylamino-5-phenyl phenazonium sulfate); poly(2-methyl-7-diethylamino-5-phenyl phenazonium chloride); poly(2-methyl-7-dimethylamino-5-phenyl phenazonium sulfate); poly(5-methyl-7-dimethylamino phenazonium acetate); poly(2-methyl-7-anilino-5-phenyl phenazonium sulfate); poly(2-methyl-7-dimethylamino phenazonium sulfate); poly(7-methylamino-5-phenyl phenazonium acetate); poly(7-ethylamino-2,5-diphenyl phenazonium chloride); poly(2,8-dimethyl-7-diethylamino-5-p-tolyl-phenazonium chloride); poly(2,5,8-triphenyl-7-dimethylamino phenazonium sulfate); and poly(7-dimethylamino-5-phenyl phenazonium chloride), by way of example and not limitation.

While various nitrite salts are usable in the practice of the invention, a preferred nitrite salt is sodium nitrite as a diazotizing agent. Another diazotizing agent that can be used in the practice of the invention is nitrosylsulfuric acid.

The reaction is typically warmed to at least 20° C. to completely produce the reaction product (polymer).

In a preferred embodiment, the metal plating bath comprises copper. Typically the copper is in the form of copper sulfate. However, other copper salts may also be used. For example, in one embodiment, as the electrolyte for the deposition of copper coatings with addition of the polymeric phenazonium compounds in accordance with the present invention, a sulfuric acid copper sulfate solution may be used of the following composition:

| | | |
|---|---|---|
| Copper sulfate | $CuSO_4 \cdot 5 H_2O$ | 125-260 g/liter |
| Sulfuric acid | $H_2SO_4$ | 20-85 g/liter |

Instead of copper sulfate, at least in part, other copper salts may be used. The sulfuric acid may be replaced partly or wholly by fluoroboric acid, phosphoric acid and/or other suitable acids. The electrolyte may be chloride-free, or this being usually advantageous for improving the luster and the leveling, it may contain chlorides, such as, alkali chlorides or hydrochloric acid, in quantities of 0.001 to 0.2 g/liter.

The concentration of the amino compound in the formic acid solution is preferably between about 100 g/l and about 200 g/l, more preferably between about 110 and about 185 g/l and most preferably between about 110 and about 122 g/l.

As discussed above, the process claimed herein does not require additional processing steps that are required in the process described for example in U.S. Pat. No. 3,743,584. For example, the process of the present invention does not require and thus does not include a neutralization step of the polymeric phenazonium compound with a base to precipitate out the polymeric phenazonium compound and additional refining and isolation steps to produce the final product.

The examples cited in U.S. Pat. No. 3,743,584 were reported in wet cake yield and properties of the substances prepared in accordance with these examples are provided below in Table 1.

TABLE 1

Properties of Substances 1-12 described in U.S. Pat. No. 3,743,584

| Substance No. | Wet cake yield | | TMW |
|---|---|---|---|
| | % | Grams | |
| 1 | 82.2 | 350 g (1M) | 426 |
| 2 | 76.4 | 300 g (1M) | 392.5 |
| 3 | 93.9 | 800 g (2M) | 426 |
| 4 | 64.1 | 20 g (0.1M) | 312 |
| 5* | 31.6 | 15 g (0.1M) | 474 |
| 6 | 28.6 | 5 g (0.05M) | 350 |
| 7 | 44.4 | 8 g (0.05M) | 360 |
| 8 | 21.325 | 4 g (0.05M) | 426.5 |
| 9 | 33.5 | 10 g (0.05M) | 497 |
| 10 | 39.1 | 8 g (0.05M) | 409.5 |
| 11 | 27.7 | 8 g (0.05M) | 578 |
| 12** | 91.2 | 750 g (2M) | 411 |

*Contaminated with $Na_2SO_4$
**Contaminated with $(NH_4)_2SO_4$

All of the above substances would also contain some alkali salts (KCl, NaCl, $K_2SO_4$, $Na_2SO_4$, $(NH_4)_2SO_4$, $NH_4Cl$, etc.).

In contrast, the process described herein does not contain a neutralizing step and, consequently, the presence of inorganic salts is eliminated.

It is hard to predict the percent monomer because of the salt content of the precipitate. However, the inventors of the present invention have determined that starting with 0.1 moles of mourner (36.45 grams) and after the process described herein is completed, the entire reaction mass is diluted to one liter of usable solution with deionzied water. The performance of this material is outstanding. If one runs the monomer through a performance sequence without the polymerization process, the results are poor at best.

When polymeric phenazonium compounds are added to the copper electrolyte as described herein, the normally crystalline-dull precipitate turns out bright in a wide current density range. Preferably the current density is maintained at a level between about 0.1 and about 8.0 ASD.

The substances produced in accordance with the present invention are also particularly suited for depositing haze-free and high-brighteners coatings in conjunction with other common luster-formers and/or wetting agents. Luster-formers and/or wetting agents, as described for example in U.S. Pat.

No. 3,743,584 can also be added to the copper electrolyte of the invention within the prescribed limits.

In addition; the concentration ratios of the individual compounds in the copper electrolyte may vary within wide limits.

The polymeric phenazonium compound produced in accordance with the process described herein can be used in the acid copper electrolyte solution at a concentration of between about 0.0001 to 0.5 g/liter, preferably of between about 0.002 and about 0.015 g/l.

Example 1

36.45 grams (0.01 moles) of an amino compound $C_{21}H_{21}N_4Cl$ (2-methyl-3-amino-5-phenyl-7-dimethylamino phenazonium chloride), available from several dyestruffs manufacturers, was dissolved in approximately 300 milliliters of 90% by weight formic acid. The solution is then cooled to between about −10 and 0° C. and the diazotizing solution (7.59 grams sodium nitrite dissolved in 25.00 grams deionized water, approximately 0.11 moles) is slowly added while maintaining the temperature within the specifed range. After the addition is complete, the reaction mass is stirred for about 2 hours at the specified temperature. An y excess nitrous acid was then destroyed by mixing the solution with 1.20 grams of sulfamic acid dissolved in 10 grams of deionized water. When the solution was warmed to about 20° C., there was very little to no outgassing observed.

The reaction is now complete and the dye concentrate is diluted to one liter with deionized water and mixed for four hours. It can now be used directly in the acid copper electrolyte without any additional intermediate steps.

Comparative Example 36.45 grams (0.01 moles) of an amino compound (2-methyl-3-amino-5-phenyl-7-dimethylamino phenazonium chloride) was dissolved in 423 ml of deionized water and then suspended with 210 ml of 37% hydrochloric acid (12.0 N solution). Thereafter, the solution was diazotized by mixing with 7.59 grams of sodium nitrite dissolved in 35.00 grams of deionized water. The excess nitrous acid is then destroyed by mixing the solution with 1.20 grams of sulfamic acid dissolved in 10.00 grams of deionized water. The solution was warmed to about 20° C.

However, significant outgassing is observed. After the nitrogen evolution has come to an end, the dye is neutralized with a solution of 315.00 grams of 45% potassium hydroxide mixed with 95.32 grams of deionized water. The neutralized dye is then filtered out of solution in the form of a precipitate, which is dried in an oven and then ground to a fine powder. Finally, the resulting dye is dissolved in sulfuric acid and then diluted with deionized water for the bath make up.

The dried polymeric phenazonium product also contained residual inorganic salts. Therefore, when making the intended product in hydrochloric acid and then neutralizing with sodium or potassium to form either sodium chloride or potassium chloride, one needs to avoid a salt/product ratio that exceeds plating bath consumption.

As described herein, the process of the present invention produces a polymeric phenazonium compound that can be more simply produced, requires fewer processing steps and does not produce any significant offgassing.

While the invention has been described above with reference to specific embodiments thereof, it is apparent that many changes, modifications, and variations can be made without departing from the inventive concept disclosed here. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A process for making a polymeric phenazonium compound and using said compound in a plating bath, said process comprising:
    (a) dissolving an effective amount of an amino compound in a formic acid solution;
    (b) adding a nitrite salt to diazotize the amino compound; and
    (c) adding sulfamic acid to neutralize any excess nitrous acid that may be formed in step b);
        whereby a polymeric phenazonium compound is produced;
        wherein the amino compound comprises an amino compound selected from the group consisting of 2-methyl-3-amino-7-dimethylamino-5-phenyl-phenazonium sulfate, 3-amino-6-methyl-7-dimethylamino-5-phenyl-phenazonium hydrogen sulfate, 2-methyl-3-amino-7-diethylamino-5-phenyl-phenazonium chloride, 3-amno-dimethylamino-5-methyl hydrogen sulfate, 2-methyl-3-amino-7-dimethylamino-phenazonium hydrogen sulfate, 3-amino-7-methlamno-5-phenylphenazonium acetate, 2-phenyl-3-amino-7-ethylamino-5-phenyl-phenazonium chloride, 1,2,6,9-tetrametyl-3-amno-7-diethylamino-5-phenylphenazonium hydrogen sulfate, 2-8-dimethyl-3-amino-7-diethylamino-5-phenyl-phenazonium hydrogen sulfate, 2,8-dimethyl-3-amino-7-diethylamino-5-tolyl-phenazonium chloride, and 2,9-diphenyl-3-amino-6-metyl-7-dimethylamino-5-phenyl-phenazonium hydrogen sulfate;
    (d) adding said polymeric phenazonium compound to a plating bath.

2. The process of claim 1, wherein the nitrite salt is sodium nitrite.

3. The process according to claim 1, wherein the amino compound is dissolved in the formic acid at a temperature of between about −10 about 0° C.

4. The process according to claim 1, wherein the concentration of the amino compound in the formic acid solution is between about 100 g/l and about 200 g/l.

5. The process according to claim 1, wherein the concentration of the amino compound in the formic acid solution is between about 120 g/l and about 185 g/l.

6. The process according to claim 1, wherein the process of producing the polymeric phenazonium compound does not include a step of neutralizing the polymeric phenazonium compound with a base.

* * * * *